(12) United States Patent
Thiem et al.

(10) Patent No.: US 6,858,183 B2
(45) Date of Patent: Feb. 22, 2005

(54) APPARATUS FOR TREATING OBJECTS

(75) Inventors: Stefan Thiem, Heidelberg (DE); Stefan Kuenkel, Karlsruhe (DE); Eric Barth, Leimen (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 418 days.

(21) Appl. No.: 09/931,600

(22) Filed: Aug. 16, 2001

(65) Prior Publication Data

US 2002/0031445 A1 Mar. 14, 2002

(30) Foreign Application Priority Data

Aug. 22, 2000 (DE) .......................................... 100 41 228

(51) Int. Cl.[7] .............................................. G01N 35/00
(52) U.S. Cl. ............................. 422/63; 422/67; 422/10; 422/103; 436/43; 436/46
(58) Field of Search ....................... 436/43, 46; 422/63, 422/65, 67, 100, 103; 435/283.1, 287.3

(56) References Cited

U.S. PATENT DOCUMENTS

| | | | | |
|---|---|---|---|---|
| 3,837,795 A | * | 9/1974 | Becker et al. ................. | 436/46 |
| 3,976,028 A | * | 8/1976 | Howells et al. ............. | 118/702 |
| 4,141,312 A | * | 2/1979 | Louder et al. .............. | 118/702 |
| 4,569,647 A | * | 2/1986 | McCormick ................ | 425/117 |
| 4,738,824 A | * | 4/1988 | Takeuchi ...................... | 422/63 |
| 4,911,098 A | * | 3/1990 | Tabata ......................... | 118/423 |
| 5,049,510 A | * | 9/1991 | Repasi et al. ............... | 436/176 |
| 5,573,727 A | * | 11/1996 | Keefe ........................... | 422/63 |
| 5,601,650 A | * | 2/1997 | Goldbecker et al. ........ | 118/697 |
| 5,895,628 A |   | 4/1999 | Heid et al. .................... | 422/65 |
| 6,017,495 A | * | 1/2000 | Ljungmann ................... | 422/65 |
| 6,080,363 A | * | 6/2000 | Takahashi et al. ............ | 422/65 |
| 6,635,225 B1 | * | 10/2003 | Theim et al. .................. | 422/65 |

* cited by examiner

Primary Examiner—Maureen M. Wallenhorst
(74) Attorney, Agent, or Firm—Hodgson Russ LLP

(57) ABSTRACT

An apparatus for treating objects, in particular cytological or histological specimens, having multiple processing stations and a transport device for delivering the objects into and out of the processing stations, is characterized in that at least one running-water station (1), having an inflow (2) and an outflow (3), is provided as a processing station.

20 Claims, 4 Drawing Sheets

APPARATUS FOR TREATING OBJECTS

CROSS REFERENCE TO RELATED APPLICATIONS

This invention claims priority of the German patent application 100 41 228.9 filed Aug. 22, 2000 which is incorporated by reference herein.

FIELD OF THE INVENTION

The invention concerns an apparatus for treating objects, in particular cytological or histological specimens, having multiple processing stations and a transport device for delivering the objects into and out of the processing stations.

BACKGROUND OF THE INVENTION

The reader is referred, purely by way of example, to EP 0 849 582 A2. This document discloses a generic apparatus for treating objects, in particular cytological or histological specimens. In this, cytological or histological specimens are conveyed by way of an object carrier or basket to an automatic stainer, the automatic stainer comprising multiple processing stations.

The generic apparatus known from EP 0 849 582 A2 also already comprises processing stations that can be used as running-water stations. In addition to a inflow, a defined outflow is provided therein. Regulation of the inflow is also not accomplished therein, so that particularly with very small objects, very considerable volumes of water are necessary.

SUMMARY OF THE INVENTION

It is the object of the present invention to configure and further develop an apparatus for treating objects, in particular cytological or histological specimens, in such a way that a running-water treatment with the smallest possible volumes of water is possible.

The aforesaid object is achieved by a generic apparatus for treating objects, in particular cytological or histological specimens, that is characterized in that at least one running-water station, having a preferably regulated inflow and an outflow, is provided as a processing station.

What has been recognized according to the present invention is firstly that for running-water treatment, a separate running-water station, which by all means can be regarded as a further processing station, is to be provided. This running-water station comprises a preferably regulated inflow and a separate outflow, thus making possible metered infeed and discharge of the running water.

Concretely, the running-water station comprises a pan into which at least one container, serving for immersion of an object or of an object carrier carrying an object, is insertable. Ultimately the container serves to receive the running water on the one hand and the object carrier on the other hand, the object carrier being, for the sake of simplicity, suspended or inserted into the container.

The container that receives the water and the object carrier is embodied similarly to the containers of the processing stations, for example can have the same dimensions. In the discussion below, reference is made to additional configurations of the container serving as the running-water station.

The pan receiving the container or containers stands on feet, so that it is spaced away from the bottom of the housing. It is thereby possible to equip the pan with supply lines from the underside.

It is furthermore advantageous if the pan has a separate holding device for the insertion of several containers at a time. For that purpose, the holding device could concretely comprise two or three bars, notched or punched out in the edge region, which are arranged so that they form one or two rows. Into the rows, i.e. between the bars, the containers are insertable in one or two rows or insertable in corresponding arrangements. A locking system, for example by way of brackets associated with the containers, is certainly possible. The containers can moreover have, in the edge region, notches for centered suspension of the object carriers.

In very particularly advantageous fashion, each of the containers inserted in the pan is connected to a water supply system and has, considered of itself, an overflow. The overflow of each container can be implemented by the fact that the container has, at a defined height, openings for water to emerge. A maximum fill level is thereby defined.

The outflow of the individual containers, especially with regard to the water that has emerged from the overflow, is collected in the pan and discharged together. A separate connector fitting for drainage of all the outflow is preferably provided in the edge region of the pan.

As already mentioned earlier, for the water supply system to the containers, a separate connector is provided for each container; the connectors can be associated with a common connector rail. In this context, the connector rail could be configured in such a way that it serves for emplacement and connection and quasi-automatic connection of the containers, so that a container simply needs to be emplaced onto the connector rail.

Several connector rails at a time can be provided inside the pan, and each connector rail can receive or connect, for example, up to six containers. It is thus possible for multiple groups of containers, emplaced in each case on connector rails, to be provided.

For easy water connection to the containers, the connector rail has for each container a connector opening into which the container is insertable with a connector fitting. A complementary configuration is also possible.

The connector openings of the connector rails are supplied with water by way of valves, preferably by way of solenoid valves. Be it noted at this juncture that what is fundamentally at issue here is a water supply system, but other solutions, reagents, or the like can be delivered. Ultimately the term "water" in this context represents any suitable fluid; instead of the actual rinsing, it is also entirely possible for any treatment taking place in a flowing medium to be accomplished.

The valves are preferably embodied as 3/2-way valves, both filling and emptying of the containers being possible by way of the valves depending on the valve position. Ultimately the valves can allow fresh water to flow in, close off the flow connection, or permit flow out of the containers.

At least one of the valves and thus also at least one of the containers could have a separate inflow and optionally a separate outflow. A provision of this kind is advantageous if, for example, one of the containers is to be supplied or rinsed with distilled water. Other applications with different fluids are conceivable.

It is advantageous in principle if several valves have a common inflow and a common outflow. In such a case the valves can be combined into a valve rail, the valves being flow-connected to the connector openings of the connector rail via lines running preferably below the pan.

In additionally advantageous fashion, the outflow provided in the pan is connected to a central outlet line. It is also conceivable for the outflow to be fed into a collection vessel.

In terms of specific monitoring or regulation of the running-water station, it is further advantageous if a sensor that detects the fill level in the pan is provided in the pan. If the outflow out of the pan should be clogged, an actuation of the valve could take place if a defined fill level is detected or if the fill level is exceeded, so that normal water infeed is shut off.

BRIEF DESCRIPTION OF THE DRAWINGS

There are various ways of advantageously embodying and developing the teaching of the present invention. The reader is referred, for that purpose, on the one hand to the claims subordinate to claim 1, and on the other hand to the explanation below of an exemplary embodiment of the invention with reference to the drawings. In conjunction with the explanation of a preferred exemplary embodiment of the invention with reference to the drawings, an explanation is also given of generally preferred embodiments and developments of the teaching. In the drawings:

DETAILED DESCRIPTION OF THE INVENTION

Figure 1:
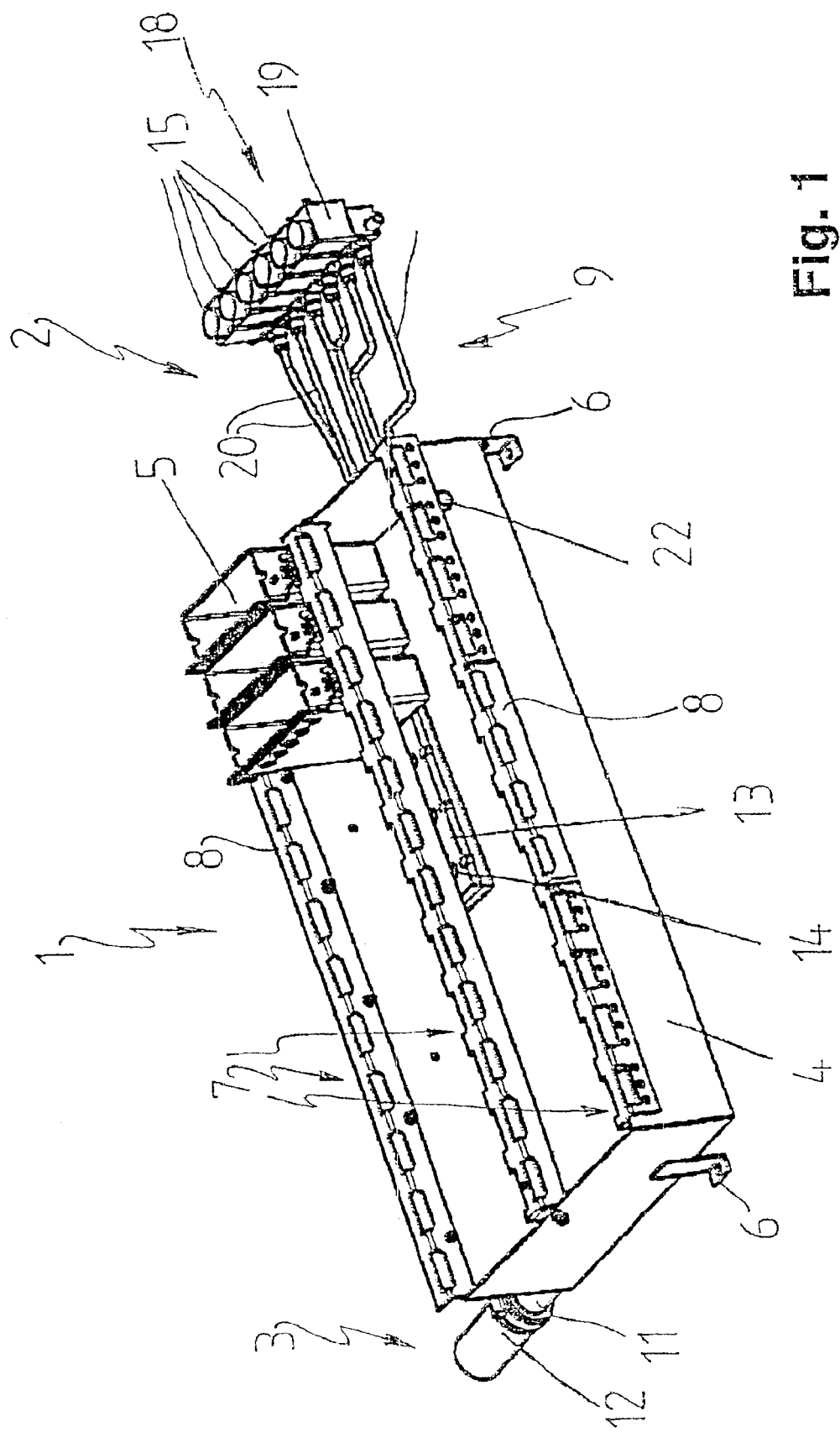
FIG. 1 shows, in a schematic view, an exemplary embodiment of a running-water station according to the present invention for use in an automatic stainer, a total of three containers being inserted into the pan and emplaced onto a connector rail.

FIG. 1 shows a portion of an apparatus for treating objects, in particular cytological or histological specimens, there being provided therein several processing stations (not shown in the Figure) and a transport device for delivering the objects into and out of the processing stations.

What is shown here concretely is a running-water station 1 for an apparatus of the kind under discussion here or for an automatic stainer, running-water station 1 serving as a processing station and having an inflow 2 and an outflow 3. Running-water station 1 is regulated, in terms of inflow 2 and optionally in terms of outflow 3, so that a minimum volume of running water is necessary.

Figure 2:
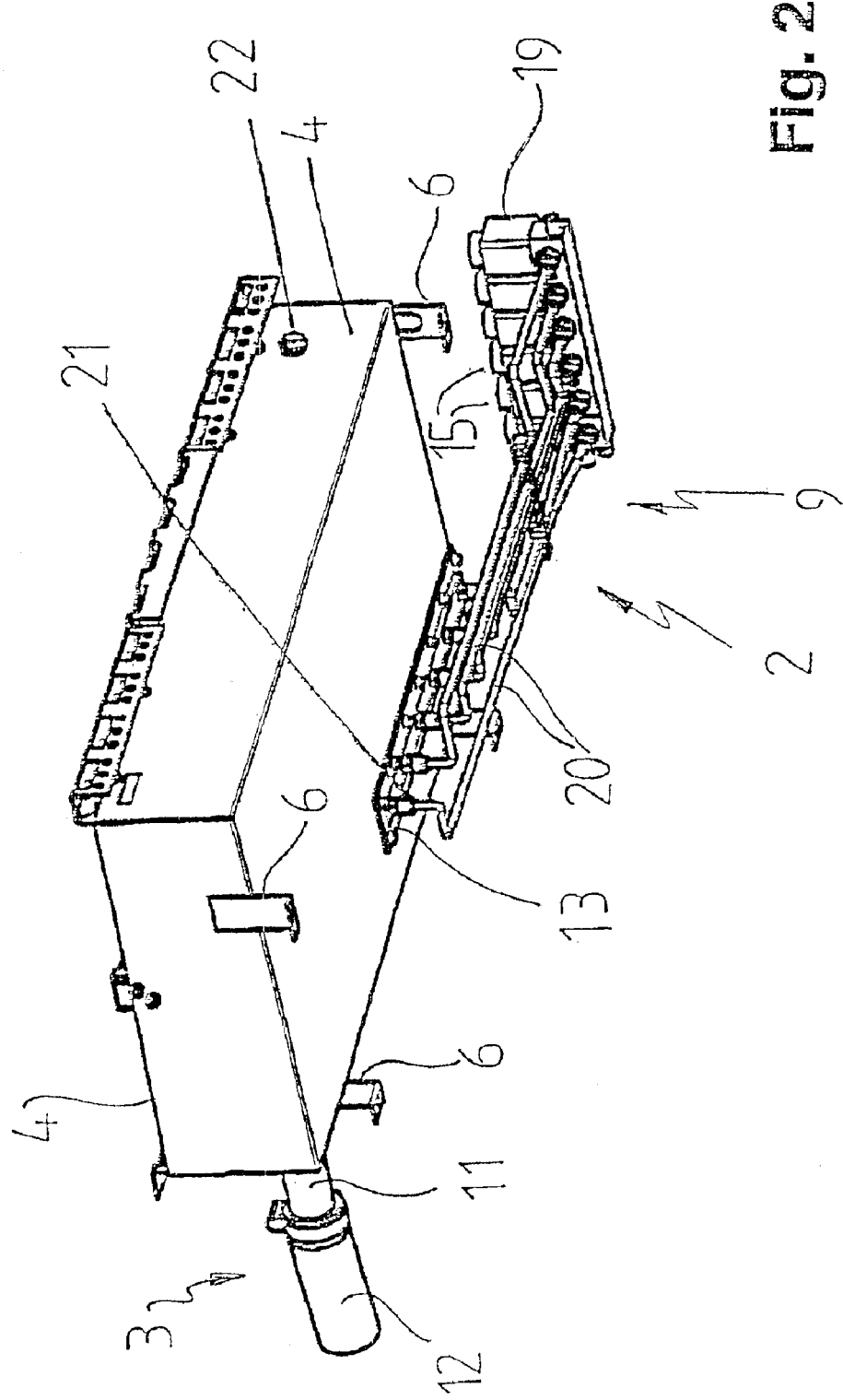
FIG. 2 shows, in a schematic view from below, the subject matter of FIG. 1.

FIGS. 1 and 2 show clearly that running-water station 1 comprises a pan 4 into which containers 5, serving for immersion of an object or of an object carrier carrying an object, are inserted. In the exemplary embodiment shown in FIG. 1, three containers 5 (of the shape shown) are inserted, arrangements being made for a total of six containers. Containers 5 are embodied similarly to the containers of the other processing stations.

FIGS. 1 and 2 furthermore indicate that pan 4 stands on feet 6, thus preventing direct contact with the bottom group of the housing of the automatic stainer. With this provision it is moreover possible for supply lines to run below pan 4.

It is also evident from FIG. 1 that pan 4 comprises a holding device 7 for the insertion of multiple containers 5. Concretely, holding device 7 comprises two bars 8 punched out in the upper region, between which the containers can be set or inserted in two rows. As already mentioned previously, in the exemplary embodiment selected here only one row of holding device 7 is occupied, specifically by a total of three containers 5.

It is furthermore essential that each of containers 5 inserted in pan 4 is connected to a water supply system 9 and has an overflow 10. The outflow is collected within pan 4 and drained via pan 4, an outflow fitting 11 being connected for that purpose to an outflow line 12.

Figure 3:
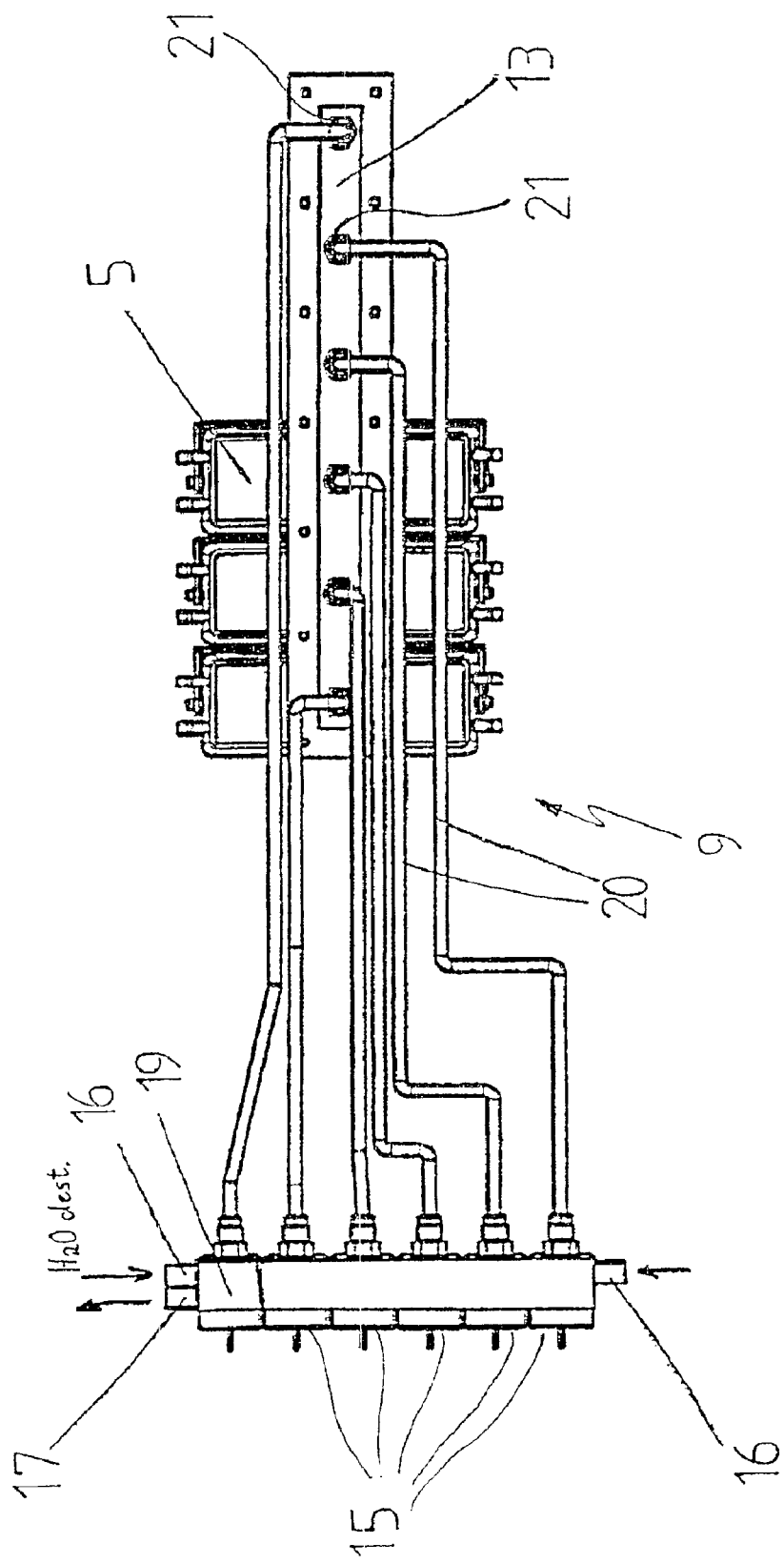
FIG. 3 shows, in a schematic view from below, the subject matter of FIG. 1 but without the pan.
Figure 4:
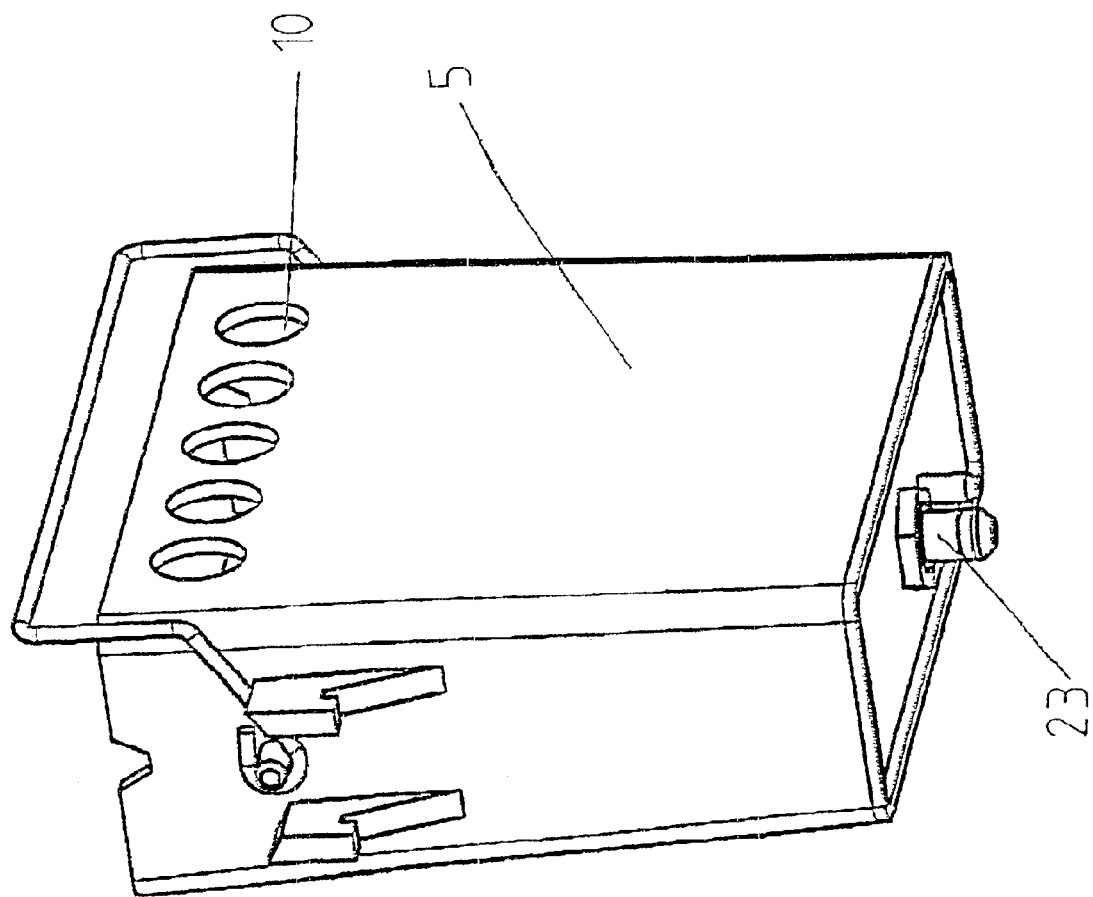
FIG. 4 shows an exemplary embodiment of a container for insertion into the pan and onto the connector rail.

It is evident from FIGS. 1, 2, and 3 that a connector rail 13 is provided in pan 4, connector rail 13 serving for emplacement and connection of containers 5. Connector rail 13 has, for each container 5 that is to be emplaced, a connector opening 14 that is supplied with water via a valve 15, which in the exemplary embodiment selected here is embodied as a solenoid valve. Concretely, valve 15 is embodied as a 3/2-way valve, both filling and emptying of container 5 being possible via valve 15.

In the exemplary embodiment shown in the Figures, several valves 15 have a common inflow 16 and outflow 17, valves 15 being combined into a valve rail 18. One of the valves, which is labeled with the reference character 19, serves for separate delivery of distilled water, outflow 17 once again being designed in common with the other valves.

FIGS. 1 through 3 furthermore indicate that valves 15, 19 are flow-connected via hose lines 20 to connector points 21 below connector rail 13. This ensures a supply of rinse water. Concretely, valves 15, 19 are flow-connected via hose lines 20 to connector openings 14, and thereby also to connector fittings 23 of container 5; rinse water can be both supplied and drained via hose line 20.

In addition, a sensor 22 that serves to detect the fill level in pan 4 is provided inside pan 4. If the maximum fill level defined by the position of sensor 22 is exceeded, valves 15, 19 can be actuated so that water delivery is shut off. This effectively prevents pan 4 from overflowing.

In conclusion, be it noted very particularly that the exemplary embodiment discussed above serves for exemplary discussion of the teaching claimed, but does not limit it to the exemplary embodiment.

Parts List

1 Running-water station
2 Inflow (of running-water station)
3 Outflow (of running-water station)
4 Pan
5 Container
6 Foot (of pan)
7 Holding device (in pan)
8 Bar (of holding device)
9 Water supply system
10 Overflow (of container)
11 Outflow fitting (of pan), outflow
12 Outflow line
13 Connector rail (in pan)
14 Connector opening (in connector rail)
15 Valve
16 Inflow (of valve)
17 Outflow (of valve)
18 Valve rail
19 Valve (for distilled water)
20 Hose line
21 Connection point
22 Sensor (in pan)
23 Connector fittings (of containers)

What is claimed is:

1. In an apparatus for treating cytological or histological specimens of a type having a plurality of conventional processing stations and a transport device for delivering said specimens into and out of said plurality of processing stations, the improvement comprising:

at least one running-water station having an inflow and an outflow is provided as a processing station, wherein said running water station comprises a pan and a plurality of containers inserted into said pan, each of said plurality of containers including a connector fitting on a bottom wall thereof for coupling said container to a water supply system, and said pan including a connector rail having a plurality of connector openings spaced therealong for respectively receiving said connector fittings of said plurality of containers.

2. The improvement as defined in claim 1, wherein said inflow is a regulated inflow.

3. The improvement as defined in claim 1, wherein said plurality of containers of said running-water station are embodied similarly to containers of said plurality of processing stations.

4. The improvement as defined in claim 1, further comprising feet for supporting said pan.

5. The improvement as defined in claim 1, wherein said pan has a holding device for holding the plurality of containers.

6. The improvement as defined in claim 5, wherein said holding device comprises a pair of spaced bars between which said plurality of containers can be supported in a row.

7. The improvement as defined in claim 5, wherein each of said plurality of containers is connected to the water supply system and has an overflow.

8. The improvement as defined in claim 7, wherein said overflow from each of said plurality of containers communicates with said pan.

9. The improvement as defined in claim 7, wherein a plurality of connector rails are provided in said pan.

10. The improvement as defined in claim 1, wherein said connector openings of said connector rail are supplied with water by way of a plurality of respective valves.

11. The improvement as defined in claim 10, wherein said plurality of valves are solenoid valves.

12. The improvement as defined in claim 10, wherein said plurality of valves are 3/2-way valves for enabling both filling and emptying of said plurality of containers by way of said plurality of valves.

13. The improvement as defined in claim 10, wherein one of said plurality of valves has an inflow separate from an inflow leading to others of said plurality of valves.

14. The improvement as defined in claim 10, wherein more than one of said plurality of valves share a common inflow and a common outflow.

15. The improvement as defined in claim 10, further comprising a valve rail into which said plurality of valves are combined.

16. The improvement as defined in claim 10, further comprising a plurality of fluid lines for connecting said plurality of valves to respective connector openings for flow communication.

17. The improvement as defined in claim 16, wherein said fluid lines are arranged to run below said pan.

18. The improvement as defined in claim 10, further comprising a sensor arranged to detect a fill level in the pan.

19. The improvement as defined in claim 18, wherein said sensor is connected to said plurality of valves, whereupon detection of a defined fill level said plurality of valves are actuated so that water infeed is shut off.

20. The improvement as defined in claim 1, wherein said pan includes an outflow connected to an outlet line.

* * * * *